US008507748B2

(12) United States Patent
Grosveld

(10) Patent No.: US 8,507,748 B2
(45) Date of Patent: *Aug. 13, 2013

(54) METHOD FOR THE PRODUCTION OF A SINGLE HEAVY CHAIN ANTIBODY

(75) Inventor: Frank Grosveld, Rotterdam (NL)

(73) Assignee: Erasmus Universiteit Rotterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/830,589

(22) Filed: Jul. 6, 2010

(65) Prior Publication Data

US 2011/0004948 A1    Jan. 6, 2011

Related U.S. Application Data

(63) Continuation of application No. 10/693,308, filed on Oct. 24, 2003, now abandoned, which is a continuation of application No. PCT/IB02/02303, filed on Apr. 24, 2002.

(30) Foreign Application Priority Data

Apr. 24, 2001  (GB) .................................. 0110029.6

(51) Int. Cl.
*C12P 21/00*    (2006.01)
*A01K 67/00*    (2006.01)

(52) U.S. Cl.
USPC .................................... 800/4; 800/6; 800/18

(58) Field of Classification Search
USPC .................................................... 800/4, 6, 18
See application file for complete search history.

(56) References Cited

U.S. PATENT DOCUMENTS

| 5,545,807 | A | * | 8/1996 | Surani et al. ...................... 800/6 |
| 5,625,126 | A | | 4/1997 | Lonberg et al. |
| 5,849,992 | A | | 12/1998 | Meade et al. |
| 5,874,299 | A | | 2/1999 | Lonberg et al. |
| 2002/0147312 | A1 | | 10/2002 | O'Keefe et al. |
| 2003/0093820 | A1 | | 5/2003 | Green et al. |
| 2005/0070014 | A1 | | 3/2005 | Maruyama et al. |
| 2009/0307787 | A1 | * | 12/2009 | Grosveld et al. ................... 800/6 |

FOREIGN PATENT DOCUMENTS

| EP | 0368684 B2 | 9/2004 |
| EP | 1199575 B1 | 7/2006 |
| WO | WO99/42077 A3 | 8/1999 |
| WO | WO02/12437 A3 | 2/2002 |
| WO | WO02/070648 A2 | 9/2002 |
| WO | WO02/085944 A2 | 10/2002 |
| WO | WO03/000737 A3 | 1/2003 |
| WO | WO03/097812 A2 | 11/2003 |
| WO | WO2004/049794 A3 | 6/2004 |
| WO | WO2007/096779 A3 | 8/2007 |

OTHER PUBLICATIONS

Nguyen et al (Molecular Immunology, 1999, 515-524.*
Davies et al (Protein Eng. 1996, 531-537.*
Raju et al Glycobiology, 2000, 10, 477-486.*
Hochepied et al Stem Cells, 2004, 22, 441-447; abstract.*
Keefer (Animal Reproduction Science 82-83: 5-12, 2004.*
Janessens et al (Proc. National Academy of Science, 2006, 15130-15130.*
Wagner et al abstract Nucleic Acids Res. 1994; 22(8):1389-93.*
Riechmann et al J Immunol Methods. 1999; 231(1-2): 25-38.*
De Genst et al, Dev Comp Immunol. 2006; 30(1-2): 187-98.*
Hamers-Casterman et al, Nature, 363:446-448, 1993.*
Xu et al (Immunity 2000 13, 37-45.*
Nguyen et al, Immunology, 2003, 109:93-101.*
Zou et al (Journal of Immunology, 2005, 175:3769-3779.*
Bond, et al., Contributions of CDR 3 to VHH Domain Stability and the Design of Monobody Scaffolds for Naive Antibody Libraries, J. Mol. Biol., vol. 332, pp. 643-655, 2003.
Bruggemann, et al., "A Repertoire of Monoclonal Antibodies with Human Heavy Chains from Transgenic Mice", Proc. Natl. Acad. Sci. USA, vol. 86, pp. 6709-6713, Sep. 1989.
Bruggemann, et al., "Strategies for Expressing Human Antibody Repertoires in Transgenic Mice", Immunology Today, vol. 17, No. 8, pp. 391-397, 1996.
Cameron, E.R., "Recent Advances in Transgenic Technology", Molecular Biotechnology, vol. 7, pp. 253-265, 1997.
Chauveau, et al., "Cutting Edge: Ig Heavy Chain 3' HIS-4 Directs Correct Spatial Position-Independent Expression of a Linked Transgene to B Lineage Cells", Journal of Immunology, vol. 163, pp. 4637-4641, 1999.
Davies, et al., 'Camelising' Human Antibody Fragments: NMR Studies on VH Domains, FEBS (Federation of European Biochemical Societies) Letters, vol. 339, No. 3, pp. 285-290, 1994.
Davies, et al., "Antibody VH Domains as Small Recognition Units", Biotechnology, vol. 13, pp. 475-479, 1995.
Davies, et al., "Single Antibody Domains as Small Recognition Units: Design and in vitro Antigen Selection of Camelized, Human VH Domains with Improved Protein Stability", Protein Engineering, vol. 9, No. 6, pp. 531-537, 1996.
Davies, et al., "Affinity Improvement of Single Antibody VH Domains: Residues in all Three Hypervariable Regions Affect Antigen Binding" Immunotechnology 2, pp. 169-179, 1996.
De Genst, et al., "Strong in Vivo Maturation Compensates for Structurally Restricted H3 Loops in Antibody Repertoires", J. Biol. Chem, vol. 280, Issue 14, pp. 14114-14121, Apr. 8, 2005.
De Genst, et al., "Antibody Repertoire Development in Camelids", Development & Comparative Immunology, vol. 30, pp. 187-198, 2006.
Ebert, et al., "A Moloney MLV-Rat Somatotropin Fusion Gene Produces Biologically Active Somatotropin in a Transgenic Pig", Molecular Endocrinology, vol. 2, pp. 277-283, 1988.
Eck, S. , et al., "Gene-Based Therapy", Goodman & Gilman's The Pharmacological Basis of Therapeutics Chapter 5, Section 1, General Principles, New York; McGraw-Hill, pp. 77-101, 2001.
Forrester, et al., "Dependence of Enhancer-Mediated Transcription of the Immunoglobulin µ Gene on Nuclear Matrix Attachment Regions", Science, vol. 265, pp. 1221-1225, Aug. 26, 1994.
Gallo, et al., "The Human Immunoglobulin Loci Introduced into Mice V(D) and J Gene Segment Usage Similar to that of Adult Humans", Eur. J. Immunol., vol. 30, pp. 534-540, 2000.

(Continued)

*Primary Examiner* — Anoop Singh
(74) *Attorney, Agent, or Firm* — Saul Ewing LLP; Doreen Y. Trujillo

(57) ABSTRACT

The present invention relates to a method for the generation of single chain immunoglobulins in a mammal. In particular, the present invention relates to a method for the generation of single chain camelid VHH antibodies in a mammal which undergo the process of class-switching and affinity maturation found within antibody producing B cells. Single chain antibodies generated using the method of the present invention and the uses thereof are also described.

6 Claims, 1 Drawing Sheet

(56) References Cited

OTHER PUBLICATIONS

Gillies, et al., "A Tissue-specific Transcription Enhancer Element is Located in the ajor Intro of a Rearranged Immunoglobulin Heavy Chain Gene", Cell, vol. 33, pp. 717-728, 1983.

Green, et al., Antigen Specific Human Monoclonal Antibodies from Mice Engineered with Human 1g Heavy and Light Chain YACs, Nature Genetics, vol. 7, pp. 13-21, May 1994.

Grosschedi, et al., "Introduction of a µ Immunoglobulin Gene into the Mouse Germ line: Specific Expression in Lymphoid Cells & Synthesis of Functional Antibody", Cell, vol. 38, pp. 647-758, 1984.

Grosschedi, et al., "Cell-Type Specificity of Immunoglobulin Gene Expression is Regulated by at Least Three DNA Sequence Elements", Cell, vol. 41, pp. 885-897, 1985.

Grosveld, et al., "Position-Independent, High-Level Expression of the Human [Beta]-Globin Gene in Transgenic Mice", Cell, vol. 51, pp. 75-985, Dec. 24, 1987.

Hammer, et al., "Genetic Engineering of Mammalian Embryos", Journal of Animal Science, vol. 63, pp. 269-278, 1986.

Hamers-Casterman, et al., "Naturally Occurring Antibodies Devoid of Light Chains", Nature, vol. 363, pp. 446-448, Jun. 3, 1993.

Hasan, et al., "Incomplete Block of B Cell Development and Immunoglobulin Production in Mice Carrying the µMT Mutation on the BALB/c Background", Eur. J. Immunol., vol. 32, pp. 3463-3471, 2002.

Hochepied, et al., "Breaking the Species Barrier: Derivation of Germline-Competent Embryonic Stem Cells from *Mus spretus* X C57BL/6 Hybrids", Stem Cells, vol. 22, pp. 441-447, 2004.

Houdebine, Louis-Marie, "Production of Pharmaceutical Proteins from Transgeenic Animals", Journal of Biotechnology, vol. 34, pp. 269-287, 1994.

Houdebine, et al., "Transgenic Animal Bioreactors", Transgenic Research, vol. 9, pp. 305-320, 2000.

Hu, et al., "Regulation of Germline Promoters by the Two Human Ig Heavy Chain 3' α Enhancers", The Journal of Immunology, vol. 164, pp. 6380-6386, 2000.

Imam, et al., "Modification of Human β-globin Locus PAC Clones by Homologous Recombination in *Escherichia coli*", Nucleic Acids Research, vol. 28, No. 12, pp. i-vi, 2000.

Jakobovits, A., "Humanizing the Mouse Genome", Current Biology, vol. 4, No. 8, pp. 761-763, 1994.

Janssens, et al., "Generation of heavy-chain-only Antibodies in Mice", PNAS, vol. 103, No. 41, pp. 15130-15135 and supplementary material on-line, 2006.

Jaton, et al., "Recovery of Antibody Activity upon Reoxidation of Completely Reduced Polyalanyl Heavy Chain and Its Fd Fragment Derived from Anti-2,4-dinitrophenyl Antibody", Biochemistry, vol. 7, No. 12, pp. 4185-4195, Dec. 1968.

Jefferis, Royston, "Glycosylation of Recombinant Antibody Therapeutics", Biotechnol. Prog., vol. 21, No. 1, pp. 11-16, 2005.

Keefer, C.L., "Production of Bioproducts through the Use of Transgenic Animal Models", Animal Reproduction Science, vol. 82-83, pp. 5-12, 2004.

Kellerman, et al., "Antibody Discovery: The Use of Transgenic Mice to Generate Human Monoclonal Antibodies for Therapeurics", Pharmaceutical Biotechnology, pp. 593-597.

Kitamura, et. al., "A B Cell-deficient Mouse by Targeted Disruption of the Membrane Exon of the Immunoglobulin µ Chain Gene", Nature, vol. 350, pp. 423-426, Apr. 4, 1991.

Kolb, et al., "Insertion of a Foreign Gene into the β-casein Locus by Cre-mediated Site-specific Recombination", Gene, vol. 227, pp. 21-31, 1999.

Kuroiwa, et al., "Manipulation of Human Minichromosomes to Carry Greater Than Megabase-sized Chromosome Inserts", Nature Biotechnology, vol. 18, pp. 1086-1090, Oct. 2000.

Kuroiwa, et al., "Cloned Transchromosomic Calves Producing Human Immunoglobulin", Nature Biotechnology, vol. 20, pp. 889-894, Sep. 2002.

Li, et al., "Locus Control Regions coming of age at a decade plus", Trends in Genetics, vol. 15, No. 10, pp. 403-408, Oct. 1999.

Lieberson, et al., "Immunoglobulin Gene Transcription Ceases Upon the Deletion of a Distant Enhancer", The EMBO Journal, vol. 14, No. 24, pp. 6229-6238, 1995.

Lillico, et al., "Transgenic Chickens as Bioreactors for Protein-based Drugs", Drug Discovery Today, vol. 10(3), pp. 191-196, 2006.

Mills, et al., "Enhancer Complexes Located Downstream of Both Human Immunoglobulin Cα Genes", The Journal of Experimental Medicine, vol. 186, pp. 845-858, 1997.

Madisen, et al., "Identification of a Locus Control Region in the Immunoglobulin Heavy-Chain Locus that Deregulates c-myc Expression in Plasmacytoma and Burkitt's Lymphoma Cells", Genes & Development, vol. 8, pp. 2212-2226, 1994.

Moreadith, et al., "Gene Targeting in Embryonic Stem Cells: The New Physiology and Metabolism", J. Mol. Med., vol. 75, pp. 208-216, 1997.

Mullins, et al.,"Transgenesis in the Rat and Larger Animals", Journal of Clinical Investigation, vol. 97, No. 7, pp. 1557-1560, 1996.

Murray, et al., "Genetic Modification of Animals in the Next Century", Theriogenology, vol. 51, pp. 149-159, 1999.

NCBI, "*Lama glama* Imunoglobulin Heavy Chain Variable Domain (VHH1) Gene, Partial CDS", Accession No. AF305944, Dated Mar. 1-15, 2001.

Nguyen, et al., "Loss of Splice Consensus Signal is Responsible for the Removal of the Entire CH1 Domain of the Functional Camel IGG2A Heavy-chain Antibodies", Molecular Immunology, vol. 36, pp. 515-524, 1999.

Nguyen, et al., "Heavy-chain Only Antibodies Derived from Dromedary are Secreted and Displayed by Mouse B Cells", Immunology, vol. 109, pp. 93-101, 2003.

Paul, W.E., "B Lymphocyte Development and Biology", Fundamental Immunology, 6th Editio, Excerpt-Chapter 7, pp. 238-261, 2008.

Pettersson, et al., "A Second B Cell-specific Enhancer 3' of the Immunoglobulin Heavy-Chain Locus", Nature, vol. 344, pp. 165-168, Mar. 8, 1990.

Pettersson, et al., "Temporal Control of IgH Gene Expression in Developing B Cells by the 3' Locus Control Region", Immunobiology, vol. 198, pp. 236-248, 1997.

Raju, et al., "Species-specific variation in glycosylation of IgG: evidence for the species-specific sialylation and branch-specific galactosylation and importance for engineering recombinant glycoprotein therapeutics", Glycobiology, vol. 10, pp. 477-486, 2000.

Riechmann, et al., "Single Domain Antibodies: Comparison of Camel VH and Camelised Human VH Domains", Journal of Immunological Methods, vol. 231, No. 1-2, pp. 25-38, 1999.

Saffery, et al., "Strategies for Engineering Human Chromosomes with Therapeutic Potential", The Journal of Gene Med., vol. 4, pp. 5-13, 2002.

Sen, et al., "Multiple Nuclear Factors Interact with the Immunoglobulin Enhancer Sequences", Cell, vol. 47, pp. 705-716, Aug. 29, 1986.

Sigmund, Carl D., "Viewpoint: Are Studies in Genetically Altered Mice Out of Control?", Arterioscler Thromb Vase Biol., vol. 20, pp. 1425-1429, Jun. 2000.

Sitia, et al., "Developmental Regulation of IgM Secretion: The Role of the Carboxy-Terminal Cysteine", Cell, vol. 60, pp. 781-790, Mar. 9, 1990.

Spinelli, et al., "The Crystal Structure of a llama heavy Chain Variable Domain", Nature Structural Biology, vol. 3, No. 9, pp. 752-757, Sep. 1996.

Stice, et al., "Cloning: New Breakthroughs Leading to Commercial Opportunities", Theriogenology, vol. 49, pp. 129-138, 1998.

Stroubolulis, J. et al., Developmental regulation of a complete 70-kb human β-globin locus in transgenic mice, Genes & Dev.., vol. 6, pp. 1857-1864, 1992.

Tuaillon, N., "Repertoire Analysis in Human Immunoglobulin Heavy Chain Minilocus Transgenic, ;µMT/µMT Mice", Molecular Immunology, vol. 32, pp. 221-231.

Wagner, et al., "Antibodies Generated from Human Immunoglobulin Miniloci in Transgenic Mice", Nucleic Acids Res., vol. 22(8), pp. 1389-1393, 1994.

Ward, et al., "Binding Activities of a Reperetoire of Single Immunoglobulin Variable Domains Secreted from *Escherichia coli*", Nature, vol. 341, pp. 544-546, Oct. 12, 1989.

Weill, et al., "Galt Versus Bone Marrow Models of B Cell Ontogeny", Developmental and Comparative Immunology, vol. 22, No. 3, pp. 379-385, 1998.

Weill, et al., Allelic Exclusion: Lesson from GALT Species, Seminars in Immunology, vol. 14, pp. 213-215, 2002.

Wolf, et al., "Nuclear Transfer in Mammals: Recent Developments and Future Perspectives", Journal of Biotechnology, vol. 65, pp. 99-110, 1998.

Wright, et al., "Effect of Glycosylation on Antibody Function: Implications for Genetic Engineering", Trends in Biotechnology, pp. 26-32, 1997.

Xu, et al., "Diversity in the CDR3 Region of VH is Sufficient for Most Antibody Specificities", Immunity, vol. 13, pp. 37-45, Jul. 2000.

Yanagimachi, et al., "Cloning: Experience from the Mouse and Other Animals", Molecular and Cellular Endocrinology, vol. 187, pp. 241-248, 2002.

Zou, T AL., "Expression of a Dromedary Heavy Chain-only Antibody and B Cell Development in the Mouse", The Journal of Immunology, vol. 175, pp. 3769-3779, 2005.

International Search Report based on PCT/IB02/02424, Dated Dec. 6, 2002.

* cited by examiner

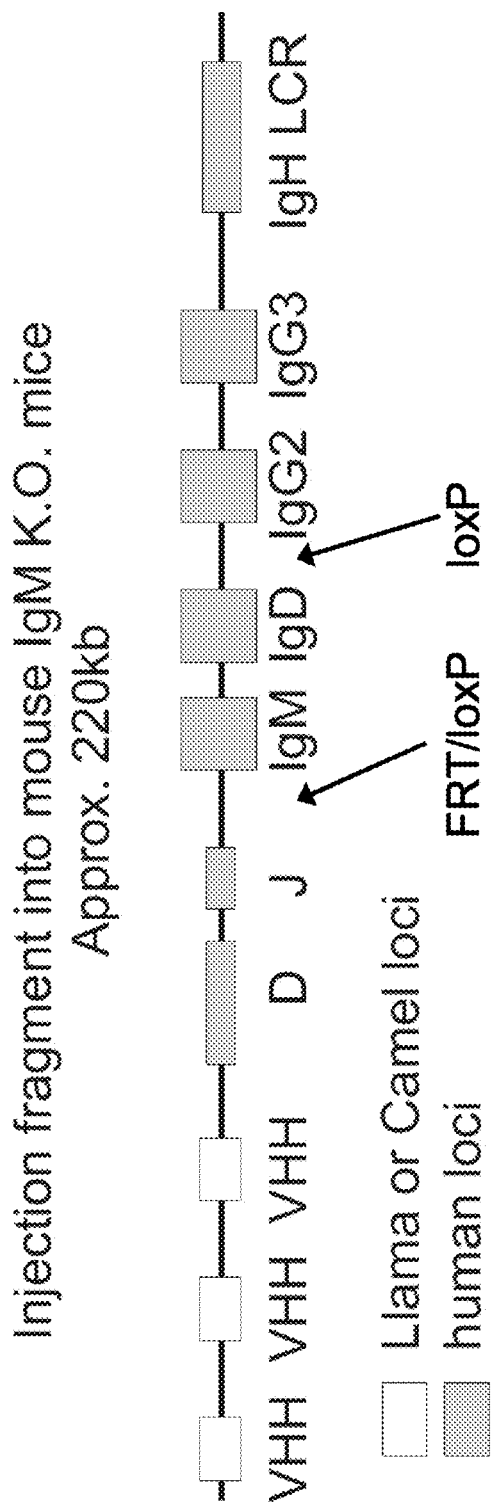

METHOD FOR THE PRODUCTION OF A SINGLE HEAVY CHAIN ANTIBODY

CROSS-REFERENCE TO RELATED APPLICATIONS

This application is a continuation of application Ser. No. 10/639,308, filed Oct. 23, 2004, which is a continuation of PCT Application Serial No. PCT/IB02/02303, filed Apr. 24, 2002, which claims priority under 35 U.S.C. §119 to Great Britain Application Serial No. 0110029.6, filed Apr. 24, 2001, all of which are incorporated by reference in their entireties.

The present invention relates to a method for the generation of single chain immunoglobulins in a mammal. In particular, the present invention relates to a method for the generation of single chain camelid VIM antibodies in a mammal. Single chain antibodies generated using the method of the present invention and the uses thereof are also described.

BACKGROUND TO THE INVENTION

The antigen binding domain of an antibody comprises two separate regions: a heavy chain variable domain (VH) and a light chain variable domain ($V_L$: which can be either $V_{kappa}$ or $V_{lambda}$). The antigen binding site itself is formed by six polypeptide loops: three from VII domain (H1, H2 and H3) and three from $V_L$ domain (L1, L2 and L3). A diverse primary repertoire of V genes that encode the VH and $V_L$ domains is produced by the combinatorial rearrangement of gene segments. The VH gene is produced by the recombination of three gene segments, VH, D and $J_H$. In humans, there are approximately 51 functional VH segments (Cook and Tomlinson (1995) *Immunol Today,* 16: 237), 25 functional D segments (Corbett et al. (1997) *J. Mol. Biol.,* 268: 69) and 6 functional $J_H$ segments (Ravetch et al. (1981) *Cell,* 27: 583), depending on the haplotype. The VH segment encodes the region of the polypeptide chain which forms the first and second antigen binding loops of the VH domain (H1 and H2), whilst the VH, D and $J_H$ segments combine to form the third antigen binding loop of the VH domain (H3). The $V_L$ gene is produced by the recombination of only two gene segments, $V_L$ and $J_L$. In humans, there are approximately 40 functional $V_k$ segments (Schäble and Zachau (1993) *Biol. Chem. Hoppe-Seyler,* 374: 1001), 31 functional Vλ segments (Williams et al. (1996) *J. Mol. Biol.,* 264: 220; Kawasaki et al. (1997) *Genome Res.,* 7: 250), 5 functional $J_K$ segments (Hieter et al. (1982) *J. Biol. Chem.,* 257: 1516) and 4 functional $J_λ$ segments (Vasicek and Leder (1990) *J. Exp. Med.,* 172: 609), depending on the haplotype. The $V_L$ segment encodes the region of the polypeptide chain which forms the first and second antigen binding loops of the $V_L$ domain (L1 and L2), whilst the $V_L$ and $J_L$ segments combine to form the third antigen binding loop of the $V_L$ domain (L3). Antibodies selected from this primary repertoire are believed to be sufficiently diverse to bind almost all antigens with at least moderate affinity. High affinity antibodies are produced by "affinity maturation" of the rearranged genes, in which point mutations are generated and selected by the immune system on the basis of improved binding.

The heavy chain locus contains a large number of variable chain genes (VH; in fact not complete genes but comprising a first coding exon plus transcriptional start site) that are recombined onto two short coding regions D and J (known as VDJ recombination) which procede the exons that code for the constant region of the heavy chain Cμ to give a complete antibody heavy chain gene known as IgM. Subsequently a class switch takes place where the variable part is recombined with another constant region that is located downstream of the IgM constant region to give IgD, IgG, IgA and IgE (coded for by the exons of the various Cδ,Cγ,Cα,Cε located downstream of the gene for Cμ. The intervening constant regions are deleted in the process. A similar process takes place in the light gene loci, first the κ locus, and when this does not lead to a productive antibody in the λ locus (for review see Rajewski, K., Nature 381, p 751-758, 1996; for an extensive review, see the textbook Immunobiology, Janeway, C., Travers, P., Walport, M., Capra. J., Current Biology Publications/Churchill Livingstone/Garland Publishing, fourth edition, 1999, ISBN 0-8153-3217-3).

Camelids (camels, dromedary and llamas) contain, in addition to normal heavy and light chain antibodies (2 light chains and 2 heavy chains in one antibody), single chain antibodies (containing only heavy chains). These are coded for by a distinct set of VH segments referred to as VHH genes. Antigen binding for single chain antibodies is different from that seen with conventional antibodies, but high affinity is achieved the same way, i.e. through hypermutation of the variable region and selection of the cells expressing such high affinity antibodies (affinity maturation). The VH and VHH are interspersed in the genome (i.e. they appear mixed in between each other). The identification of an identical D segment in a VH and VHH cDNA suggests the common use of the D segment for VH and VHH. Natural VHH containing antibodies are missing the entire $C_H1$ domain of the constant region of the heavy chain. The exon coding for the $C_H1$ domain is present in the genome but is spliced out due to the loss of a functional splice acceptor sequence at the 5' side of the $C_H1$ exon. As a result the VDJ region is spliced onto the $C_H2$ exon. When a VHH is recombined onto such constant regions ($C_H2$, $C_H3$) an antibody is produced that acts as a single chain antibody (i.e. an antibody of two heavy chains without a light chain interaction). Binding of an antigen is different from that seen with a conventional antibody, but high affinity is achieved the same way, i.e. through hypermutation of the variable region and selection of the cells expressing such high affinity antibodies.

The structure of isolated VH domains has been determined using NMR and X-ray crystallography techniques (Spinell et al, (1996), Nat Structural biol. 3, 752). Data show that the Immunoglobulin fold is well preserved in Camelid VHH domains. Two beta sheets (one with four and one with five beta-strands) are packed against each other and stabilised by a conserved intradomain disulphide bond between C22 and C92. The side of the camel VHH domain corresponding to the VL interface of the normal VH in an Fv has a quite different architecture. Compared to the human VH, four amino acid substitutions are located in this region.

From a survey of all human and mouse VH antigen binding loop structures, it is apparent that there are only a restricted number of possible conformations. Three and four different conformations are described for the first and second antigen binding loop respectively. These canonical structures are determined by the length of the loop and the presence of particular residues at key positions. The H3 loop is extremely variable in length and sequence (Wu et al (1993) Proteins: structure, funct and genet., 16, 1). Surprisingly, the antigen binding loop of camel VH domains deviate from the canonical loop definitions of human and mouse VHH domains. This deviation could not be predicted as the loop length and the residues at the key positions are very similar between camel VH and human VH. The additional canonical loop structures in camel VH domains make the structural repertoire of their paratope larger than that of VH domains in Fv fragments from conventional antibodies. Moreover, the hypervariable region around the first antigen binding loop is enlarged compared with human or mouse antibodies. It is thought that the extension of the first hypervariable region and concomitant enlarged antigen binding surface compared to that of a VH in a conventional antibody compensates in part for the absence of a $V_L$ domain (Riechmann, L. & Muyldermans, S (1999), 231 25-38).

A single domain camelid VHH antibody as well as being more suitable for structural analysis than the larger heavy and light chain antibody molecules, also provides a small and efficient antigen binding unit. Such an antibody has many and varied therapeutic potential. In addition, it has been found that camelid single chain antibodies can bind antigens which are inaccessible to antibodies possessing both heavy and light chains. It is thought that this ability is due to the presence of a large protruding third hypervariable loop of 10 amino acids or more which can insert into cavities of antigen surfaces. This is especially significant as the catalytic site of an enzyme is often located at the largest cavity on their protein surface. (Ladowski, R. A (1996). Protein Science 5, 2438). Such sites are not normally immunogenic for conventional antibodies (Novotny, J et al, (1986) Proc Nat Acad Sci USA, 83, 226). In the structure of the camel VHH cAb-Lys3, the 24 residue H3 loop penetrates deeply into the active site of lysozyme (Transue, T. R et al (1998) Prot: Structure, Funct and Genet, 32, 515), showing that Camel heavy chain antibodies have the potential to form specific enzyme inhibitors.

Recently, isolated Camelid VHH domains have been generated in bacteria (Riechmann, L et al. Journal of Immunological Methods 231 (1999), 25-38). However bacterial expression systems have the disadvantage that they do not perform post-translational modifications. Such modifications, in particular glycosylation events, are crucial for the effective functioning of antibodies, particularly in an in vivo environment.

In the same study, the genes for Camel VHH domains were inserted into expression vectors and expressed in Cos cells to generate multi-domain proteins. In one example, an intact single heavy chain only antibody was generated by cloning a particular camel VHH in front of the hinge and effector function domains of human IgG1. The expression in Cos cells has the advantage over bacterial expression systems that post-translational modification events occur in these cells. Consistent with this was the finding that these antibodies were fully active in antigen binding. The DNA for the generation of these constructs is generally isolated from mature (ie those which have undergone affinity maturation) antibodies generated from B cells. Although these single chain antibodies expressed in mammalian cells in an in vitro environment can bind to one or more antigens, they cannot undergo the processes of class (isotype) switching and affinity maturation (hypermutation). Thus the single chain antibodies expressed in Cos cells do not undergo the process of antibody evolution as those naturally occurring antibodies generated within a mammal. It is this process of antibody evolution which results in the production of specific antibodies which bind with high affinity. Thus, there remains a need in the art for a method allowing the generation of single chain VHH antibodies in a mammal such that the normal processes of antibody evolution can take place.

In addition Camelid single chain antibodies have also been selected and expressed using phage display technology. (Riechmann, L. & Davies, S. J. Biomol. NMR, 6, 141). Again though, the antibody constructs are generated from nucleic acid isolated from mature B cells or spleen, and therefore as with the case above, the antibodies expressed do not undergo class switching and somatic hypermutation (affinity maturation) which is necessary for the production of specific antibodies which bind to their antigen with selectivity and high affinity.

The present inventors realised that if they could understand the mechanism by which camelid single chain antibody molecules evolve (by class-switching and affinity maturation) during early antibody development in B cells, then this system may be recreated in vivo. This would allow the generation of vast quantities of an evolved single chain antibody for structural, therapeutic and diagnostic applications.

SUMMARY OF THE INVENTION

Antibody molecules which comprise both heavy and light chains switch classes during B-cell development. Developing B cells in the bone marrow first express membrane bound IgM. During development secretory IgG is expressed. In the case of antibodies possessing both light and heavy chains, a J region is recombined onto a Cµ region to produce an IgM comprising VH, D and J regions. The IgM producing cell further matures by switching to a different heavy chain constant region to produce IgA for example. The mechanism of recombination involves a pseudo light chain which recombines with the VH part of IgM, the pseudo-light chain being present during the early B cell lineage.

The present inventors realised that understanding the mechanism by which single chain antibodies switch classes and/or undergo affinity maturation (antibody evolution) during pre B-cell development would allow a VHH locus as herein defined to be generated which resulted in the production of a specific single chain VHH antibody which undergoes a process of evolution similar or the same as that of camelid antibodies produced in their native environment.

Thus, in a first aspect the present invention provides a method for the production of a VHH single heavy chain antibody in a mammal comprising the step of expressing a heterologous VHH heavy chain locus in that mammal.

Preferably the VHH heavy chain locus comprises:
(a) at least one VHH region each comprising one VHH exon, at least one D region each comprising one D exon and at least one J region each comprising one J exon, wherein the VHH region, the D region and the J region are capable of recombining to form VDJ coding sequence,
(b) a constant heavy chain region comprising at least one Cγ constant heavy chain gene, and which when expressed does not express a functional CH1 domain nor a functional CH4 domain,
(c) at least one recombination sequence (rss) capable of recombining a J region of step (a) directly with a Cγ constant heavy chain gene of step (b).
and which locus when expressed is capable of forming a complete single heavy chain IgG molecule (scIgG).

In a further aspect, the present invention provides a method for the production of a camelised VH single heavy chain antibody in a mammal comprising the step of expressing a camelised VH heavy chain locus in that mammal Preferably, the camelised VH heavy chain locus comprises:
(a) a VH region each comprising one VH exon which is mutated such that the nucleic acid sequence is the same as a camelid VHH exon (a 'camelised VH exon'), a D region comprising one D exon and a J region comprising one J exon, wherein the VH region, the D region and the J region are capable of recombining to form VDJ coding sequence, and (b) a constant heavy chain region comprising at least one Cγ constant heavy chain gene, and which when expressed does not express a functional CH1 domain nor a functional CH4 domain, (c) at least one recombination sequence (rss) capable of recombining a J region of step (a) directly with a Cγ constant heavy chain gene of step (b).

and which locus when expressed is capable of forming a complete single heavy chain IgG molecule (scIgG).

The present inventors have shown that in the case of single heavy chain antibodies, class switching occurs to form scAb (a complete single heavy chain antibody polypeptide chain). This mechanism involves recombining the J region of step (a) directly with a Cγ heavy chain region gene of the constant heavy chain region of step (b), preferably in the bone marrow resulting in the generation of a scIgG (single chain IgG molecule). The presence of the recombination signal sequence (rss) in the construct, therefore permits the connection of the J region of step (a) directly to the Cγ gene of step (b).

In the context of the present invention, the mammal is not a human. The transgenic mammal is advantageously smaller than a camelid and easier to maintain and immunise with desired antigens. Ideally, the transgenic mammal is a rodent, such as a rabbit, guinea pig, rat or mouse. Mice are especially preferred. Alternative mammals, including goats, sheep, cats, dogs and other domestic or wild mammals, may also be employed.

Advantageously heavy chain loci endogenous to the mammal are deleted or silenced when a single chain antibody is expressed according to the method of the present invention. Suitable techniques for the later are described in WO00/26373 or WO96/33266 and (Li and Baker (2000) Genetics 156(2): 809-821; Kitamura and Rajewsky (1992); Kitamura and Rajewsky, (1992) Nature 356, 154-156).

The term a 'VHH single heavy chain antibody' according to the present invention means an antibody molecule which is composed only of heavy chains (generally two) and does not comprise any light chains. Each heavy chain comprises a variable region (encoded by VHH, D and J exons) and a constant region. The constant region further comprises a number of CH (constant heavy chain domains), advantageously it comprises two: one CH2 domain and one CH3 domain encoded by a constant region gene. A VHH single chain antibody as herein defined does not possess a functional CH1 domain and also lacks a functional CH4 domain. It is the lack of a functional CH1 domain (which in conventional antibodies possesses the anchoring place for the constant domain of the light chain) which accounts for the inability of the heavy chain antibodies according to the present invention to associate with light chains to form conventional antibodies.

The term 'a camelised VH single heavy chain antibody' according to the present invention means an antibody molecule which is composed only of heavy chains (generally two) and does not comprise any light chains. Each heavy chain comprises a variable region (encoded by 'a camelised VH exon/s', D and J exon/s) and a constant region. The constant region comprises at least one constant region gene. Each constant region gene comprises a number of constant region exons, each exon encoding a constant region CH domain. Generally, the constant region comprises two CH domains: one CH2 domain and one CH3 domain. A camelised VH single chain antibody as herein defined does not possess a functional CH1 domain, in addition it also lacks a functional CH4 domain. It is the lack of a functional CH1 domain (which in conventional antibodies possesses the anchoring place for the constant domain of the light chain) which accounts for the inability of the heavy chain antibodies according to the present invention to associate with light chains to form conventional antibodies.

In the context of the present invention, the term 'heterologous' means a VHH heavy chain locus as herein described which is not endogenous to that mammal. That is in the case where the mammal is a camelid ie a camel or a llama, then the expression is of a VHH locus which is not normally found within a camel or llama respectively.

A 'VHH heavy chain locus' according to the present invention is comprised of a 'VHH region', a 'J region', a 'D region' and a 'constant heavy chain region'. Each VHH region comprises one VHH exon, each J region one J exon and each D region one D exon, and each heavy chain constant region comprises one or more heavy chain constant region genes. In addition each VHH region essentially does not comprise one or more functional VH exons.

A 'VHH exon/region' in the context of the present invention describes a naturally occurring VHH coding sequence such as those found in Camelids and any homologue, derivative or fragment thereof as long as the resultant exon/region recombine with a D exon/region, a J exon/region and a constant heavy chain region (which comprises several exons) according to the present invention to generate a VHH single chain antibody as herein defined, when the nucleic acid is expressed.

A 'camelised VH heavy chain locus' according to the present invention is comprised of a 'a camelised VH region' as herein defined, a 'J region', a 'D region' and a 'constant heavy chain region'. Each camelised VH region comprises one camelised VH exon, each J region one J exon and each D region one D exon and each heavy chain constant region comprises one or more heavy chain constant region exons.

A 'camelised VH exon/region' in the context of the present invention describes a naturally occurring VH coding sequence derived from mammals other than Camelids for example a human which has been mutated such that the sequence is the same as that of a Camelid exon. A camelised VH exon according to the present invention also includes within its scope any homologue, derivative or fragment of the exon as long as the exon/region can recombine with a D region/exon, a J region/exon and a constant heavy chain region comprising one or more exons according to the present invention to generate a camelised VH single chain antibody as herein defined.

VHH and VH exons may be derived from naturally occurring sources or they may be synthesised using methods familiar to those skilled in the art and described herein.

Likewise in the context of the present invention the terms 'a D exon' and 'a J exon' include naturally occurring sequences of D and J exons which are found in Camelids or other species of mammals. The terms D exon and J exon also include within their scope derivatives, homologues and fragments thereof as the resultant exon can recombine with the remaining components of a heavy chain antibody locus as herein described (either camelised VH or VHH) to generate a single chain antibody as herein described. D and J exons/regions may be derived from naturally occurring sources or they may be synthesised using methods familiar to those skilled in the art and described herein.

In addition, a heavy chain antibody locus according to the present invention (either VHH or camelised VH) comprises a region of DNA encoding a constant heavy chain polypeptide (a constant heavy chain region).

Each constant heavy chain region essentially comprises at least one constant region heavy chain gene which is Cγ, so that generation of single chain IgG can occur. Each constant heavy chain gene comprises one or more constant heavy chain exons which may be of Camelid or non-Camelid origin and are selected from the group consisting of $C\delta$, $C\gamma_{1-4}$, $C\epsilon$ and $C\alpha_{1-2}$. Preferably, at least one heavy chain constant region exon in a heavy chain antibody locus according to the present invention is of human, mouse or rabbit origin. Advantageously, at least one $C\gamma$ heavy chain exon is of human origin. When expressed the constant heavy chain region lacks a functional CH1 and CH4 domain which are present in dual chain antibodies. Advantageously, only one or more $C\gamma2$ and/or $C\gamma3$ genes with modified (non-functional) CH1 domains are present in the constant heavy chain region of the present invention.

A 'constant heavy chain region exon' ('$C_H$ exon') as herein defined includes the sequences of naturally occurring $C_H$ exons such as those found in camelids or humans or other mammals including rabbits and mice. The term '$C_H$ exon' also includes within its scope derivatives, homologues and fragments thereof in so far as the $C_H$ exon is able to form a functional single heavy chain antibody (comprising either regions encoded by VHH exons or camelised VH exons) as herein defined when it is a component of a constant heavy chain region.

Generally, $C_H$ genes comprise three or four exons ($C_H1$-$C_H4$) that encode different domains of each constant heavy chain polypeptide, with generally two polypeptides constituting a single heavy chain antibody as herein described. However, as discussed previously, VHH and camelised VH single chain antibodies do not possess an functional CH1 (containing the light chain domain anchoring region) or CH4. Thus, single heavy chain antibody loci according to the present invention possess one or more genes which do not express functional CH1 or CH4 domains. This may occur by mutation, deletion substituted or other treatment of the CH1 and CH4 exons of the constant heavy region gene.

In a preferred embodiment of the invention a single chain VHH locus comprises at least one constant heavy chain gene wherein the nucleic acid encoding the CH1 and the CH4 domain is mutated, deleted or substituted or otherwise treated so that the constant heavy chain of expressed VHH single chain antibodies as herein defined does not contain a functional CH1 domain and a CH4 domain.

For the avoidance of doubt, the term 'rabbit origin' or 'human origin' as referred to above, means that the nucleic acid sequence of one or more exons comprising a heavy chain antibody locus (either camelised VH or VHH) according to the present invention is the same as one or more naturally occurring rabbit or human antibody locus exons. One skilled in the art will appreciate that these exons may be derived from natural sources or may be synthesised using methods familiar to those skilled in the art and described herein.

Each VHH or 'camelised VH region' comprises one VHH exon or 'camelised VH exon' respectively. Each J region and D region comprises one J and D exon respectively. Preferably, each heavy chain locus comprises more than one, more than 2, more than 3, more than 4, more than 5, more than 6 J and/or D regions/exons. Most preferably, a VHH locus or camelised VH locus according to the present invention comprises the same number of VHH exons/regions and/or D exons/regions and/or J exons/regions as those found in a Camelid.

Advantageously, the method of this aspect of the present invention is for the production of a single chain antibody by the expression of a VHH heavy chain locus or camelised VH heavy chain locus comprising one or more constant heavy chain exons of human, rabbit or mouse origin as herein defined. That is, preferably a single heavy chain antibody of the present invention is generated by the expression of a hybrid camelid/human locus or a hybrid camelid/rabbit locus or a hybrid camelid/mouse locus. In an especially preferred embodiment of this aspect of the invention, the single heavy chain locus expressed according to the method of the present invention comprises all VHH exons of Camelid origin and all D, J and constant heavy chain region exons of human origin, rabbit or mouse origin. In a further preferred embodiment of this aspect of the invention, the single heavy chain locus expressed according to the method of the present invention comprises all camelised VH exons and all D, J and constant heavy chain region exons of human origin, or rabbit or mouse origin.

In a preferred embodiments of the above aspects of the invention, the heavy chain locus further comprises one or more cassette sites enabling the direct cassetting of the locus from one vector to another. Advantageously, one or more cassette sites are located in the 5' leader sequence of the locus and/or the 3' untranslated region of the locus. Preferably, one or more cassettes sites are located in both the 5' leader sequence of the locus and the 3' untranslated region of the locus. The direct cassetting permits, for example, movement of nucleic acid into a bacterial expression vector for the addition of tags, signals and the like.

This approach of generating hybrid single heavy chain antibodies as described above maybe of particular use in the generation of antibodies for human therapeutic use as often the administration of antibodies to a species of vertebrate which is of different origin from the source of the antibodies results in the onset of an immune response against those administered antibodies. Hybrid camelid/human single chain antibodies are therefore potentially less immunogenic than Camelid single chain antibodies when administered to a human.

In the context of the present invention, the same includes substantially the same. Substantially the same means greater than 80% homologous, preferably greater than 85%, 90%, 95% homologous. More preferably greater than 96, 97, 98% homologous. Most preferably, substantially the same means that the mutated human VH region is greater than 99% homologous with a Camelid VHH region In a further aspect, the present invention provides a VHH single heavy chain antibody obtainable according to the method of the present invention wherein that part of the antibody encoded by a VHH exon is encoded by an exon of camelid origin and the remainder of the antibody molecule is encoded by exons of human origin.

In yet a further aspect, the present invention provides a VHH single heavy chain antibody obtainable according to the method of the present invention, wherein that part of the antibody encoded by a VHH exon is encoded by an exon of camelid origin and the constant heavy chain region is encoded by one or more exon/s of rabbit origin.

In a further aspect still, the present invention provides a VHH single heavy chain antibody obtainable according to the method of the present invention wherein that part of the antibody encoded by a VHH exon is encoded by an exon of camelid origin and the constant heavy chain region is encoded by one or more exon/s of mouse origin.

In yet a further aspect, the present invention provides a camelised single heavy chain antibody obtainable by the method of the present invention Advantageously, a camelised VH single heavy chain antibody according to this aspect of the present invention is entirely encoded by exons of human origin as herein defined.

In a further preferred embodiment of this aspect of the invention, a camelised VH single heavy chain antibody comprises a constant heavy chain region encoded by one or more exon/s of rabbit origin.

In a further embodiment still, a camelised VH single heavy chain antibody according to this aspect of the invention comprises a constant heavy chain region encoded by one or more exon/s of mouse origin.

Antibodies produced according to the method of the present invention have the advantage over those of the prior art in that they undergo a process of class switching which is similar or the same as that of a single chain Camelid antibody generated in its normal environment. Antibodies obtainable according to the methods of the present invention may be monoclonal or polyclonal antibodies. Advantageously, they are monoclonal antibodies. Antibodies may be generated using methods known to those skilled in the art. Advantageously hybridomas may be used for generating monoclonal antibodies. Techniques will be familiar to those skilled in the art and are described herein.

In yet a further aspect, the present invention provides a vector comprising a VHH heavy chain locus according to the present invention.

In a further aspect still, the present invention provides a vector comprising a camelised VH heavy chain locus according to the present invention.

Suitable vectors will be familiar to those skilled in the art. Advantageously, a vector suitable of inserting large amounts of nucleic acid, sufficient to encode an entire immunoglobulin heavy chain locus are preferred. Suitable vectors include yeast and bacterial artificial chromosomes such as YACs and BACs. Advantageously, the vectors are constructed so that direct cassetting of nucleic acid encoding a single heavy chain antibody locus as herein defined into a different vector can be performed. For example the reverse transcribed cDNA coding for a single heavy chain antibody may be 'cassetted' into a bacterial expression vector allowing for the addition of tags, signals or epitopes and the like.

In yet a further aspect, the present invention provides a host cell transformed with a VHH locus according to the present invention.

In a further aspect still, the present invention provides a transgenic mammal expressing a heterologous VHH heavy chain locus according to the present invention.

In yet a further aspect, the present invention provides a transgenic mammal expressing a camelised VH heavy chain locus according to the present invention.

In the context of the present invention, the term 'a transgenic mammal' does not include within its scope a transgenic human. Preferably a transgenic mammal according to the present invention is smaller than a Camelid. Preferably it is selected from the group consisting of: a mouse, rat, guinea-pig, hamster, monkey and rabbit. Advantageously, it is a mouse.

Advantageously heavy chain loci endogenous to the transgenic animal are deleted or silenced in a transgenic mammal according to the present invention. Suitable techniques for the later are described in WO00/26373 or WO96/33266 and (Li and Baker (2000) Genetics 156(2): 809-821; Kitamura and Rajewsky (1992); Kitamura and Rajewsky, (1992) Nature 356, 154-156).

Antibody producing cells may be derived from transgenic animals according to the present invention and used for example in the preparation of hybridomas for the production of VHH single chain antibodies as herein defined. In addition or alternatively, nucleic acid sequences may be isolated from transgenic mammals according to the present invention and used to produce single chain antibodies, using recombinant DNA techniques which are familiar to those skilled in the art.

Alternatively or in addition, specific single chain antibodies may be generated by immunising a transgenic animal according to the present invention.

Thus in a further aspect, the present invention provides a method for the production of single chain antibodies by immunising a transgenic mammal according to the present invention with an antigen.

In a preferred embodiment of this aspect of the invention, the mammal is a mouse.

In the context of the present invention, the term 'immunising' a mammal means administering to a transgenic mammal of the present invention an antigen such that an immune response is elicited against that antigen. Suitable methods for the immunisation of mammals will be familiar to those skilled in the art and are described herein. Suitable antigens may be naturally occurring or synthetic. Naturally occurring antigens include proteins which may be for example enzymes or cofactors, peptides and nucleic acid molecules. One skilled in the art will appreciate that this list is not intended to be exhaustive.

In a further aspect, the present invention provides the use of a single heavy chain antibody as herein described as an intracellular binding reagent.

In a further aspect, the present invention provides, the use of a single chain antibody according to the present invention as an enzyme inhibitor.

In a further aspect still, the present invention provides the use of an antibody obtainable by the method of the present invention in the preparation of a medicament for the prophylaxis and/or treatment of disease.

In a final aspect, the present invention provides the use of a heavy chain antibody locus according to the present invention in the prophylaxis or treatment of disease.

BRIEF DESCRIPTION OF THE FIGURES

FIG. 1 shows a preferred single chain antibody locus according to the present invention.

DEFINITIONS

'A gene' comprises one or more exons coding for a complete mRNA. An 'antibody gene' comprises V, D, J exons which recombine to form a VDJ coding region and which then further recombine with a constant heavy chain region comprising one or more constant heavy chain exons. There are many sub-groups of V, D J and C exons. One particular V region has one exon, one D region has one exon, one J region has one exon and one C region has several exons. Together they from a complete gene after recombination when one V exon, one D exon, one J exon and one C region have been selected.

'Exon' and 'intron'. An Exon is a coding or messenger sequence of deoxynucleotides. That is, it is any sequence of DNA in eukaryotes that will be ultimately expressed in mature mRNA or rRNA molecules. Exons are commonly interspersed with introns. Introns are non-coding DNA sequences. That is they are DNA sequences which are not ultimately expressed in a mature RNA molecule. Introns are spliced out from newly transcribed RNA to order to generate mature mRNA.

A 'VHH heavy chain locus' according to the present invention is comprised of a 'VHH region', a 'J region/exon', a 'D region/exon' and a 'constant heavy chain region'. Each VHH region comprises one VHH exon, each J region one J exon and each D region one D exon and each heavy chain constant region comprises one or more heavy chain constant region exons.

A 'VHH exon' in the context of the present invention describes a naturally occurring VHH coding sequence such as those found in Camelids and any homologue, derivative or fragment thereof as long as the resultant exon can when a constituent of a VHH region as herein defined recombine with at least one D region, at least one J region and at least one constant heavy chain region according to the present invention to generate a VHH single chain antibody as herein defined, when the nucleic acid is expressed.

A 'camelised VH heavy chain locus' according to the present invention is comprised of one or more 'camelised VH region/s' as herein defined, one or more 'J region/s', one or more 'D region/s' and a 'constant heavy chain region'. Each camelised VH region comprises one camelised VH exon, each J region one J exon and each D region one D exon and each heavy chain constant region comprises one or more heavy chain constant region genes.

A 'camelised VH exon' in the context of the present invention describes a naturally occurring VH coding sequence derived from mammals other than Camelids for example a human which has been mutated such that the sequence is the same as that of a Camelid exon. A camelised VH exon according to the present invention also includes within its scope any homologue, derivative or fragment of the exon as long as the resultant exon can, when a constituent of a camelised VH region as herein defined recombine with at least one D region, one J region and one constant heavy chain region according to the present invention to generate a camelised VH single chain antibody as herein defined.

A 'constant heavy chain region exon' ('$C_H$ exon') as herein defined includes the sequences of naturally occurring $C_H$ exons such as those found in camelids or humans or other mammals including rabbits and mice. The term '$C_H$ exon' also includes within its scope derivatives, homologues and fragments thereof in so far as the $C_H$ exon is able to form a functional single heavy chain antibody as herein defined when it is a component of a constant heavy chain region. Generally, $C_H$ exons are of four different types ($C_H1$-$C_H4$) that encode different portions (domains) of each constant heavy chain polypeptide. However, VHH and camelised VH single chain antibodies according to the present invention do not possess a functional CH1 domain (containing the light chain domain anchoring region) nor do they possess a functional CH4 domain. There are a number of sub-groups of constant heavy chain region exons. Different antibody classes possess different CH exons for instance, IgM molecules possess one or more Cμ constant region exons and IgG molecules possess one or more Cγ exons.

The term a 'VHH single heavy chain antibody' according to the present invention means an antibody molecule which is composed only of heavy chains (generally two) and does not comprise any light chains. Each heavy chain comprises a variable region (encoded by VHH, D and J exons) and a constant region. The constant region further comprises a number of CH domains encoded by constant heavy region exons, generally it comprises two: one CH2 domain and one CH3 domain. A VHH single chain antibody as herein defined does not possess a functional CH1 domain nor a functional CH4 domain. It is the lack of a functional CH1 domain (which in conventional antibodies possesses the anchoring place for the constant domain of the light chain) which accounts for the inability of the heavy chain antibodies according to the present invention to associate with light chains to form conventional antibodies. The sub-class of antibodies known as scIgG2 and/or scIgG3 comprise only Cγ2 and/or Cγ3 genes.

The term 'a camelised VH single heavy chain antibody' according to the present invention means an antibody molecule which is composed only of heavy chains (generally two) and does not comprise any light chains. Each heavy chain comprises a variable region (encoded by 'a camelised VH exon', D and J exon/s) and a constant region. The constant region encoded by constant region exons further encodes a number of CH domains, generally it comprises two: one CH2 domain and one CH3 domain. A camelised VH single chain antibody as herein defined does not possess a functional CH1 domain or a functional CH4 domain. It is the lack of a functional CH1 domain (which in conventional antibodies possesses the anchoring place for the constant domain of the light chain) which accounts for the inability of the heavy chain antibodies according to the present invention to associate with light chains to form conventional antibodies.

'Antibodies' as used herein, refers to antibodies or antibody fragments capable of binding to a selected target, and includes monoclonal and polyclonal antibodies, engineered antibodies including chimeric, CDR-grafted and humanised antibodies, and artificially selected antibodies produced using phage display or alternative techniques. Small antibody fragments possess advantageous properties for diagnostic and therapeutic applications on account of their small size and consequent superior tissue distribution.

'Antibody evolution' describes the process of class switching and affinity maturation (somatic hypermutation) which occurs during antibody development and which results in the generation of antibodies which bind selectively and with high affinity.

DETAILED DESCRIPTION OF THE INVENTION

General Techniques

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) $4^{th}$ Ed, John Wiley & Sons, Inc. which are incorporated herein by reference) and chemical methods. In addition Harlow & Lane., A Laboratory Manual Cold Spring Harbor, N.Y., is referred to for standard Immunological Techniques.

VH/h Heavy Chain Loci of the Present Invention

In a first aspect, the present invention provides a method for the production of a VHH single heavy chain antibody in a mammal comprising the step of expressing a heterologous VHH heavy chain locus in that mammal.

In a further aspect, the present invention provides a method for the production of a camelised VH single heavy chain antibody in a mammal comprising the step of expressing a camelised VH heavy chain locus in that mammal.

The construction of the various VHH heavy chain loci according to the present invention are as described in the summary of the invention.

Advantageously, a locus of the invention comprises one or more FRT (flp recombination target) sites (http://www.esb.utexus.edu), and two or more LoxP sites (which consists of two thirteen by inverted repeats separated by an 8 bp asymmetric spacer region (Brian Sauer, Methods of Enzymology; 1993, Vol 225, 890-900).

Preferably, there are at least two loxP sites in a locus according to the present invention. The presence of the FRT site/s in the locus allows the production of single copy transgenics, whilst the presence of the Lox sites allows the deletion of IgM and IgD heavy chain genes if required.

(A) Vectors

The present invention also provides vectors including a construct of the present invention. Essentially two types of vectors are provided, replication vectors and transformation vectors.

(I) Replication Vectors

Constructs of the invention can be incorporated into a recombinant replicable vector such as a BAC vector. The vector may be used to replicate the construct in a compatible host cell. Thus, in a further embodiment, the invention provides a method of making constructs of the invention by introducing a construct of the invention into a replicable vector, introducing the vector into a compatible host cell, and growing the host cell under conditions which bring about replication of the construct. The construct may be recovered from the host cell. Suitable host cells include bacteria such as *E. coli*, yeast, mammalian cell lines and other eukaryotic cell lines, for example insect Sf9 cells (baculovirus).

(II) Transformation Vectors

The constructs of the present invention may also be incorporated into a vector capable of inserting the construct into a recipient genome and thus achieving transformation. In addition to the construct of the present invention such transformation vectors may include one or more of the following components.

Promoters

The promoter is typically selected from promoters which are functional in mammalian cells, although prokaryotic promoters and promoters functional in other eukaryotic cells may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of alpha-actin, beta-actin, tubulin) or, alternatively, a tissue-specific manner (such as promoters of immunoglobulin genes). They may also be promoters that respond to specific stimuli, for example promoters that bind steroid hormone receptors. Viral promoters may also be used, for example the Moloney murine leukaemia virus long terminal repeat (MMLV LTR) promoter, the Rous sarcoma virus (RSV) LTR promoter or the human cytomegalovirus (CMV) IE promoter. It may also be advantageous for the promoters to be inducible so that the levels of expression of the heterologous gene can be regulated during the life-time of the cell. Inducible means that the levels of expression obtained using the promoter can be regulated.

In addition, any of these promoters may be modified by the addition of further regulatory sequences, for example enhancer sequences. Tissue-specific enhancers capable of regulating expression in antibody-producing cells are preferred. In to particular, the heavy-chain enhancer required for the successful activation of the antibody gene locus in vivo (Serwe, M., and Sablitzky, F., EMBO J. 12, p 2321-2321, 1993) may be included. Locus control regions (LCRs), particularly the immunoglobulin LCR, may also be used. Chimeric promoters may also be used comprising sequence elements from two or more different promoters.

Other Vector Components

In addition to a promoter and the construct, vectors of the present invention preferably contain other elements useful for optimal functioning of the vector in the mammal into which the vector is inserted. These elements are well known to those of ordinary skill in the art, and are described, for example in Sambrook et al., Molecular Cloning: A Laboratory Manual Cold Spring Harbor Laboratory Press, 1989.

Construction of Vectors

Vectors used for transforming mammalian embryos are constructed using methods well known in the art, including, without limitation, the standard techniques of restriction endonuclease digestion, ligation, plasmid and DNA and RNA purification, DNA sequencing, and the like as described, for example in Sambrook, Fritsch, and Maniatis, eds., Molecular Cloning: A Laboratory Manual., (Cold Spring Harbor Laboratory Press, Cold Spring Harbor, N.Y. [1989]). In general, vector construction will include the following steps:

a) The endogenous mouse locus is inactivated, for example using one of the published knockout procedures (eg. Kitamara, D and Rajewski K., Nature 352, p 154-156, 1992).

b) The DJ and IgM region of a suitable heavy chain region as herein described is localised as a recombinant DNA from a human PAC, BAC or YAC library and cloned as a restriction enzyme fragment, for instance a Sal1 fragment. This region also contains the heavy chain enhancer required for the successful activation of the antibody gene locus in vivo (see Serwe, M., Sablitzky, F., EMBO J. 12, p 2321-2321, 1993).

c) A number of VHH or 'camelised VH exons' are first cloned as cosmids through the construction of a suitable genomic DNA library by conventional techniques. Since the VHH exons are located among VH exons as herein described they are subsequently cloned along with the VHH exons. Thus an array of VH and VHH exons is made. This array of genes can be isolated as a MluI (or other restriction enzyme) fragment.

d) The 3' human immunoglobulin heavy chain LCR, a regulatory region required for the expression of the locus, is cloned as an SceI restriction fragment.

e) The constant region heavy chain exons are cloned as a separate restriction fragment. The $C_H1$ and/or $C_H4$ domains encoded by their respective exons are rendered non-functional by homologous recombination in bacteria (Imam et al., 2000) by removing the splice acceptor sequences of the $C_H1$ exon and/or $C_H4$ exon (Nguyen et al., ibid,).

Steps b-e provide the pieces for a 'VHH heavy chain locus' or 'a camelised VH heavy chain locus' (FIG. 3) that should take over the function of the inactivated mouse locus described under a). These loci are constructed by cloning each of the fragments in the appropriate order into a suitable vector, for example a BAC vector containing a linker region with all of the restriction sites described above (FIG. 1). Loci created according to the method of the present invention are generally in the order of 200-250 kB in size. They can be isolated and purified away from the vector by standard laboratory techniques which will be familiar to those skilled in the art. The purified nucleic acid encoding the 'VHH heavy chain locus' or 'a camelised VH heavy chain locus' according to the present invention (FIG. 3) may be subsequently introduced into fertilised mouse eggs derived from the knock-out mice described in a) by standard techniques to obtain transgenic mice expressing one or more loci according to the present invention.

Single Chain Antibodies According to the Present Invention

It will be understood that term 'a single heavy chain antibody' and 'VHH heavy chain loci' according to the present invention also include homologous polypeptide and nucleic acid sequences obtained from any source, for example related cellular homologues, homologues from other species and variants or derivatives thereof.

Thus, the present invention encompasses variants, homologues or derivatives of the single heavy chain antibodies and VHH heavy chain loci as herein described.

In the context of the present invention, a homologous sequence is taken to include an amino acid sequence which is at least 80, 85, 90, 95, 96, 97, 98, 99, 99.5, 99.6, 99.7, 99.8, 99.9% identical, preferably at least 98 or 99% identical at the amino acid level over at least 30, preferably 50, 70, 90 or 100 amino acids. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

Methods for the Production of Single Chain Antibodies According to the Present Invention (A) Transgenic Animals The loci and vectors of the present invention may be introduced into an animal to produce a transgenic animal. Thus, the present invention also provides a transgenic animal including a construct described herein.

Inserting the loci into the genome of a recipient animal may be achieved using any technique apparent to those skilled in the art, for example, microinjection. Following introduction of nucleic acid into a fertilised egg, reimplantation is accomplished using standard methods which will be familiar to those skilled in the art. Usually, the surrogate host is anaesthetised, and the eggs are inserted into the oviduct. The number of eggs implanted into a particular host will vary, but will usually be comparable to the number of offspring the species naturally produces.

Alternatively, the DNA may be introduced into embryonic stem cells (ES) cells which can be inserted into a host embryo to derive transgenic mice by standard technology.

In a further embodiment the DNA can be introduced into any cell. The nuclei of these cells are used to replace the nucleus of a fertilised egg which may be of any species to give rise to transgenic animals. This technique of nuclear transfer is familiar to those skilled in the art.

Transgenic offspring of the surrogate host may be screened for the presence of the transgene by any suitable method. Screening is often accomplished by Southern or Northern analysis, using a probe that is complementary to at least a portion of the transgene. Western blot analysis using a ligand specific for the antibody encoded by the transgene may be employed as an alternative or additional method for screening. Typically, the tissues or cells believed to express the transgene at the highest levels are tested, although any tissues or cell types may be used for this analysis.

Progeny of the transgenic mammals may be obtained by mating the transgenic mammal with a suitable partner, or by in vitro fertilisation of eggs and/or sperm obtained from the transgenic mammal. Where in vitro fertilisation is used, the fertilised embryo may be implanted into a surrogate host or incubated in vitro, or both. Where mating is used to produce transgenic progeny, the transgenic mammal may be backcrossed to a parental line. Using either method, the progeny may be evaluated for the presence of the transgene using methods described above, or other appropriate methods.

The animal may be varied provided it is a mammal. Preferably, the animal is a non-human mammal such as a rodent and even more preferably a rat or mouse. In this regard, it is also preferred that the recipient animal is incapable of producing antibodies that include light chains or at the very least has a reduced capacity to produce such antibodies. To achieve this end the recipient animal may be a "knock out" animal that is capable of having one or more of the genes required for the production of antibodies with light chains turned off or suppressed.

By using recipient animals incapable of producing antibodies that include light chains or at the very least with only a reduced capacity to produce such antibodies, the method of the present invention enables the efficient production of large quantities of single chain antibodies and antibody producing cells from a transgenic animal according to the present invention upon challenge with a given antigen.

(B) Phage Display Technology

Vectors for phage display fuse the encoded polypeptide to, e.g., the gene III protein (pIII) or gene VIII protein (pVIII) for display on the surface of filamentous phage, such as M13. See Barbas et al., *Phage Display: A Laboratory Manual*, Cold Spring Harbor Laboratory Press (2001) (ISBN 0-87969-546-3); Kay et al. (eds.), *Phage Display of Peptides and Proteins: A Laboratory Manual*, San Diego: Academic Press, Inc., 1996; Abelson et al. (eds.), *Combinatorial Chemistry*, Methods in Enzymology vol. 267, Academic Press (May 1996).

Prokaryotic hosts are particularly useful for producing phage displayed antibodies of the present invention. The technology of phage-displayed antibodies, in which antibody variable region fragments are fused, for example, to the gene III protein (pIII) or gene VIII protein (pVIII) for display on the surface of filamentous phage, such as M13, is by now well-established, Sidhu, *Curr. Opin. Biotechnol.* 11(6):610-6 (2000); Griffiths et al., *Curr. Opin. Biotechnol.* 9(1):102-8 (1998); Hoogenboom et al., *Immunotechnology*, 4(1):1-20 (1998); Rader et al., *Current Opinion in Biotechnology* 8:503-508 (1997); Aujame et al., *Human Antibodies* 8:155-168 (1997); Hoogenboom, *Trends in Biotechnol.* 15:62-70 (1997); de Kruif et al., 17:453-455 (1996); Barbas et al., *Trends in Biotechnol.* 14:230-234 (1996); Winter et al., *Ann. Rev. Immunol.* 433-455 (1994), and techniques and protocols required to generate, propagate, screen (pan), and use the antibody fragments from such libraries have recently been compiled, Barbas et al., *Phage Display: A Laboratory Manual*, Cold Spring Harbor Laboratory Press (2001) (ISBN 0-87969-546-3); Kay et al. (eds.), *Phage Display of Peptides and Proteins: A Laboratory Manual*, Academic Press, Inc. (1996); Abelson et al. (eds.), *Combinatorial Chemistry*, Methods in Enzymology vol. 267, Academic Press (May 1996), the disclosures of which are incorporated herein by reference in their entireties.

For the phage display of antibodies as herein described including fragments thereof, advantageously, they are fused to the phage g3p protein.

(C) Hybridomas

Recombinant DNA technology may be used to produce single chain antibodies according to the present invention using an established procedure, in bacterial or preferably mammalian cell culture. The selected cell culture system preferably secretes the single chain antibody product.

Multiplication of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, e.g. foetal calf serum, or trace elements and growth sustaining supplements, e.g. feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in medium LB, NZCYM, NZYM, NZM, Terrific Broth, SOB, SOC, 2×YT, or M9 Minimal Medium, and for yeast in medium YPD, YEPD, Minimal Medium, or Complete Minimal Dropout Medium.

In vitro production provides relatively pure immunoglobulin preparations and allows scale-up to give large amounts of the desired immunoglobulins. Techniques for bacterial cell, yeast or mammalian cell cultivation are known in the art and include homogeneous suspension culture, e.g. in an airlift reactor or in a continuous stirrer reactor, or immobilised or entrapped cell culture, e.g. in hollow fibres, microcapsules, on agarose microbeads or ceramic cartridges.

Large quantities of the desired immunoglobulins can also be obtained by multiplying mammalian cells in vivo. For this purpose, hybridoma cells producing the desired immunoglobulins are injected into histocompatible mammals to cause growth of antibody-producing tumours. Optionally, the animals are primed with a hydrocarbon, especially mineral oils such as pristane (tetramethyl-pentadecane), prior to the injection. After one to three weeks, the immunoglobulins are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The foregoing, and other, techniques are discussed in, for example, Kohler and Milstein, (1975) Nature 256:495-497; U.S. Pat. No. 4,376,110; Harlow and Lane, Antibodies: a Laboratory Manual, (1988) Cold Spring Harbor, incorporated herein by reference. Techniques for the preparation of recombinant antibody molecules is described in the above references and also in, for example, EP 0623679; EP 0368684 and EP 0436597, which are incorporated herein by reference.

The cell culture supernatants are screened for the desired antibodies, preferentially by immunofluorescent staining of cells expressing the desired target by immunoblotting, by an enzyme immunoassay, e.g. a sandwich assay or a dot-assay, or a radioimmunoassay.

For isolation of the antibodies, those present in the culture supernatants or in the ascitic fluid may be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/ or (immuno-)affinity chromatography, e.g. affinity chromatography with the target molecule or with Protein-A.

(3) Immunisation of a Transgenic Animal

In a further aspect, the present invention provides a method for the production of single chain antibodies according to the present invention comprising administering an antigen to a transgenic animal according to the present invention.

The single chain antibodies produced from transgenic animals of the present invention include polyclonal and monoclonal single chain antibodies and fragments thereof. If polyclonal antibodies are desired, the transgenic animal (e.g., mouse, rabbit, goat, horse, etc.) may be immunised with an antigen and serum from the immunised animal collected and treated according to known procedures. If serum containing polyclonal antibodies contains antibodies to other antigens, the polyclonal antibodies of interest can be purified by immunoaffinity chromatography and such like techniques which will be familiar to those skilled in the art. Techniques for producing and processing polyclonal antisera are also known in the art.

Uses of Single Chain Antibodies According to the Present Invention

Single chain antibodies including fragments thereof according to the present invention may be employed in in vivo therapeutic and prophylactic applications, in vitro and in vivo diagnostic applications, in vitro assay and reagent applications, and the like.

Therapeutic and prophylactic uses of single chain antibodies according to the invention involve the administration of the above to a recipient mammal, such as a human.

'Camelised VH single chain heavy chain antibodies' possess several advantages over camelid VHH single chain antibody molecules in the treatment of humans. For example camelised VH single chain antibodies possess a protein A binding site in the case of antibodies based on the VH3 gene family. In addition, camelised VH single chain antibodies are expected to show lower immunogenicity than camelid VHH single chain antibodies when administered to humans.

It will also be appreciated that 'camelised VH single heavy chain antibodies' and 'camelid VHH single heavy chain antibodies' have some different physical characteristics than conventional dual chain antibodies. For example, due to the lack of a functional CH1 heavy domain, antibodies of the present invention do not bind complement molecule C1q which is involved in activation of the classical pathway of complement.

Substantially pure single chain antibodies including fragments thereof of at least 90 to 95% homogeneity are preferred for administration to a mammal, and 98 to 99% or more homogeneity is most preferred for pharmaceutical uses, especially when the mammal is a human. Once purified, partially or to homogeneity as desired, the single to chain antibodies as herein described may be used diagnostically or therapeutically (including extracorporeally) or in developing and performing assay procedures using methods known to those skilled in the art.

The selected single chain antibodies of the present invention will typically find use in preventing, suppressing or treating inflammatory states, allergic hypersensitivity, cancer, bacterial or viral infection, and autoimmune disorders (which include, but are not limited to, Type I diabetes, multiple sclerosis, rheumatoid arthritis, systemic lupus erythematosus, Crohn's disease and myasthenia gravis), and in preventing transplant rejection. For instance, depletion of the regulatory T cells or interference with their recruitment may result in an enhanced immune response which may be of particular use in the treatment of infections which otherwise escape a normal immune response.

In addition, the selected single chain antibodies including fragments thereof maybe useful for modulating an immune response in regions of a vertebrate where they are not normally located. For example, one or more antibodies used as herein described may be perfused, injected, into a tissue of a vertebrate, using techniques known to those skilled in the art. The presence of an antibody as described herein, in such an ectopic environment may be useful in the modulation of an immune response during for example, transplant rejection and the like.

In the instant application, the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the selected antibodies of the present invention in protecting against or treating the disease are available. Methods for the testing of systemic lupus erythematosus (SLE) in susceptible mice are known in the art (Knight et al. (1978) *J. Exp. Med.*, 147: 1653; Reinersten et al. (1978) New Eng. J. Med., 299: 515). Myasthenia Gravis (MG) is tested in SJL/J female mice by inducing the disease with soluble AchR protein from another species (Lindstrom et al. (1988) Adv. Immunol., 42: 233). Arthritis is induced in a susceptible strain of mice by injection of Type II collagen (Stuart et al. (1984) Ann. Rev. Immunol., 42: 233). A model by which adjuvant arthritis is induced in susceptible rats by injection of mycobacterial heat shock protein has been described (Van Eden et al. (1988) Nature, 331: 171). Thyroiditis is induced in mice by administration of thyroglobulin as described (Maron et al. (1980) J. Exp. Med., 152: 1115). Insulin dependent diabetes mellitus (IDDM) occurs naturally or can be induced in certain strains of mice such as those described by Kanasawa et al. (1984) Diabetologia, 27: 113. EAE in mouse and rat serves as a model for MS in human. In this model, the demyelinating disease is induced by administration of myelin basic protein (see Paterson (1986) Textbook of Immunopathology, Mischer et al., eds., Grune and Stratton, New York, pp. 179-213; McFarlin et al. (1973) Science, 179: 478: and Satoh et al. (1987) J. Immunol., 138: 179).

Generally, the selected single chain antibodies of the present invention will be utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The selected single chain antibodies including fragments thereof, of the present invention may be used as separately administered compositions or in conjunction with other agents. These can include various immunotherapeutic drugs, such as cyclosporine, methotrexate, adriamycin or cisplatinum, and immunotoxins. Pharmaceutical compositions can include "cocktails" of various cytotoxic or other agents in conjunction with the selected antibodies, or T-cells of the present invention or even combinations of the selected antibodies according to the present invention.

The route of administration of pharmaceutical compositions according to the invention may be any of those commonly known to those of ordinary skill in the art. For therapy, including without limitation immunotherapy, the selected antibodies, receptors or binding proteins thereof of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter.

The dosage and frequency of administration will depend on the age, sex and condition of the patient, concurrent administration of other drugs, counterindications and other parameters to be taken into account by the clinician.

The selected antibodies, of this invention can be lyophilised for storage and reconstituted in a suitable carrier prior to use. Known lyophilisation and reconstitution techniques can be employed. It will be appreciated by those skilled in the art that lyophilisation and reconstitution can lead to varying degrees of functional activity loss and that use levels may have to be adjusted upward to compensate.

In addition, antibodies according to the present invention may be used for diagnostic purposes. For example antibodies as herein described may be generated or raised against antigens which are specifically expressed during disease states or whose levels change during a given disease states.

For certain purposes such as diagnostic or tracing purposes labels may be added. Suitable labels include but are not limited to any of the following, radioactive labels, NMR spin labels and fluorescent labels. Means for the detection of the labels will be to familiar to those skilled in the art.

Examples of suitable radioactive labels include technetium 99m ($^{99m}$Tc) or iodine-123 ($^{123}$I). Labels such as iodine-123, iodine-313, indium-111, fluorine-19, carbon-13, nitrogen-15, oxygen-17, gadolinium, manganese or iron allow detection of the label using NMR. Labels such as 11C methionine and FDG are suitable for use in the technique of positron emission tomography. Descriptions of procedures and protocols for using PET are familiar to those skilled in the art.

A suitable fluorophore is GFP or a mutant thereof. GFP and its mutants may be synthesised together with the antibodies of the present invention or target molecule by expression therewith as a fusion polypeptide, according to methods well known in the art. For example, a transcription unit may be constructed as an in-frame fusion of the desired GFP and the immunoglobulin or target, and inserted into a vector as described above, using conventional PCR cloning and ligation techniques.

Antibodies according to the present invention may be labelled with any agent capable of generating a signal. The signal may be any detectable signal, such as the induction of the expression of a detectable gene product. Examples of detectable gene products include bioluminescent polypeptides, such as luciferase and GFP, polypeptides detectable by specific assays, such as beta-galactosidase and CAT, and polypeptides which modulate the growth characteristics of the host cell, such as enzymes required for metabolism such as HIS3, or antibiotic resistance genes such as G418.

The compositions containing the present selected antibodies of the present invention or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.00005 to 5.0 mg of selected single chain antibody per kilogram of body weight, with doses of 0.0005 to 2.0 mg/kg/dose being more commonly used. For prophylactic applications, compositions containing the present selected polypeptides or cocktails thereof may also be administered in similar or slightly lower dosages.

A composition containing one or more selected antibodies according to the present invention may be utilised in prophylactic and therapeutic settings to aid in the alteration, inactivation, killing or removal of a select target cell population in a mammal. In addition, the selected repertoires of polypeptides described herein may be used extracorporeally or in vitro selectively to kill, deplete or otherwise effectively remove a target cell population from a heterogeneous collection of cells. Blood from a mammal may be combined extracorporeally with the selected antibodies, cell-surface receptors or binding proteins thereof whereby the undesired cells are killed or otherwise removed from the blood for return to the mammal in accordance with standard techniques.

In a further aspect, the present invention provides the use of a single heavy chain antibody as herein described as an intracellular binding reagent.

Antibodies of the present invention can be expressed in any cell type and may bind to and affect the function of any intracellular component. Intracellular components may be for example components of the cytoskeleton, molecules involved in gene expression and/or the regulation of expression, enzymes or molecules involved in the regulation of the function of cellular components. One skilled in the art will appreciate that this list is not intended to be exhaustive. Where for example the component is an enzyme inhibitor, an antibody of the present invention may increase or decrease the activity of the enzyme. The active site of enzymes is often located in the largest cavity on the protein surface. Such sites are not normally immunogenic for conventional antibodies (Novotny et al, (1986) Proc. Nat. Acad USA, 83, 226). The long H3 loop of single chain antibodies according to the present invention penetrates deeply into the active site of enzymes, allowing them to act as efficient enzyme inhibitors.

In particular the single chain antibodies, and/or fragments and/or compositions thereof to of the present invention may be of particular use as anti-viral and/or antibacterials in external applications, for instance in the form of creams for skin, vaginal application and so on. In addition, antibodies fragments and compositions according to the present invention may find use in treating equipment, such as places where opportunistic infections are prevalent. For example, antibodies, fragments thereof and compositions may be of particular use in hospital environments, and in particular intensive care units. Furthermore, the antibodies, fragments thereof, and compositions of the present invention may find use in the treatment of transplantation material either artificial or natural tissue. For example stents or bone marrow infected with CMV or other viruses.

In addition, other functions may be added to antibodies of the present invention such as transport peptides and/or functional moieties providing an enzymic activity, for example kinases, proteases, phosphatases, de-acetylases, acetylases, ubiquitinylation enzymes, sumolation enzymes, methylases etc. Furthermore, other antibodies may be attached to the single chain antibodies, or fragments thereof according to the present invention. Those skilled in the art will appreciate that this list is not intended to be exhaustive.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, vatrious modificattons of the described modes for carrying out the invention which are obvious to those skilled in biochemistry, molecular biology and biotechnology or related fields are intended to be within the scoop of the follwoing claims.

What is claimed is:

1. A method for the production of a single heavy chain antibody comprising:
   (i) immunizing a transgenic mouse whose genome comprises a heterologous VHH heavy chain locus with an antigen, wherein the heterologous VHH heavy chain locus comprises:
      (a) at least one VHH exon, at least one D exon and at least one J exon, wherein the VHH exon, the D exon and the J exon are capable of recombining to form a VDJ coding sequence, and wherein the VHH exon comprises a naturally occurring camelid VHH coding sequence,
      (b) at least one constant heavy chain region comprising at least one constant heavy chain gene, wherein each of said at least one constant heavy chain gene, when expressed, does not express a functional CH1 domain, and
      (c) a locus control region providing for expression of the VHH heavy chain locus specifically in B cells, wherein said mouse expresses the VHH heavy chain locus in B cells in response to antigen challenge; and
   (ii) isolating single heavy chain antibody against said antigen.

2. The method of claim 1, wherein the at least one D exon is of human origin, the at least one J exon is of human origin, and the constant heavy chain region comprising at least one heavy chain gene is of human origin.

3. The method of claim 1, wherein the at least one constant heavy chain region comprises at least one constant heavy chain gene which is not of camelid origin.

4. The method of claim 3, wherein the at least one constant heavy chain gene which is not of camelid origin is of mouse origin.

5. The method of claim 1, wherein the entire VHH heavy chain locus is of camelid origin.

6. The method of claim 1, wherein the endogenous mouse heavy chain loci are deleted or silenced.

* * * * *